United States Patent
Kaneda et al.

[11] Patent Number: 5,871,521
[45] Date of Patent: Feb. 16, 1999

[54] LASER PROBE FOR MEDICAL TREATMENT

[75] Inventors: Akira Kaneda, Osaka; Yoshiteru Ii, Izumi; Shinichi Nakahara, Ikeda; Jiro Minehisa, Suita, all of Japan

[73] Assignee: Matsushita Electric Industrial Co., Ltd., Osaka, Japan

[21] Appl. No.: 698,201

[22] Filed: Aug. 14, 1996

[30] Foreign Application Priority Data

Aug. 25, 1995 [JP] Japan ................................ 7-240885
Jan. 19, 1996 [JP] Japan ................................ 8-025808

[51] Int. Cl.⁶ .................................................. A61N 5/00
[52] U.S. Cl. ................................ 607/89; 607/92; 606/14; 606/16
[58] Field of Search ........................... 606/2, 3, 13–17; 607/88, 89, 92, 93, 100

[56] References Cited

U.S. PATENT DOCUMENTS

| | | | |
|---|---|---|---|
| 4,660,925 | 4/1987 | McCaughan, Jr. | 606/15 |
| 4,736,743 | 4/1988 | Daikuzono | 606/17 |
| 5,196,005 | 3/1993 | Doiron et al. | 606/15 |
| 5,292,320 | 3/1994 | Brown et al. | 606/17 |
| 5,330,465 | 7/1994 | Doiron et al. | 606/15 |
| 5,415,655 | 5/1995 | Fuller et al. | 606/17 |
| 5,431,647 | 7/1995 | Purcell, Jr. et al. | 606/17 |

FOREIGN PATENT DOCUMENTS 63-318933A 12/1988 Japan .

*Primary Examiner*—Jennifer Bahr
*Assistant Examiner*—Bryan K. Yarnell
*Attorney, Agent, or Firm*—Stevens, Davis, Miller & Mosher, L.L.P.

[57] ABSTRACT

A medical laser probe to be used as a laser irradiation unit in laser treatment that is performed by irradiating a living body with laser light. The laser probe irradiates laser light uniformly, utilizing laser light effectively by concentration thereof, achieving limited irradiation of laser light and taking countermeasures against stains forming on the probe. The laser probe is provided with (1) a transparent light diffuser for radiating laser light received by a light-guide fiber in the direction along the longitudinal axis of the light diffuser and in radial directions from this axis to the peripheral side surface thereof and (2) a detachable protective diffusion tube for further diffusing laser light radiated from the transparent light diffuser. A reflector may be provided between the light diffuser and the diffusion tube. Further, shielding plates may be provided on the protective diffusion tube.

18 Claims, 6 Drawing Sheets

LASER PROBE FOR MEDICAL TREATMENT

BACKGROUND OF THE INVENTION

1. Field of the Invention

The present invention relates to a probe for laser irradiation, which is used in a medical laser device for performing laser treatment by irradiating a human being or an animal with laser light or beams.

2. Description of the Related Art

With the recent advance of science and technology, applications of laser light are being developed rapidly in the field of medical treatment. Especially, internal laser treatment to be performed or provided in combination with the utilization of an endoscope is expected to come into widespread use in the future, because the internal laser treatment permits a patient to be treated without an incision and relieves a burden imposed on the physical strength of a patient. Hereinafter, a photodynamic therapy (hereunder abbreviated as PDT), which utilizes medicine in combination with laser light, will be described.

This PDT is a treatment of a focus or nidus such as a tumor, to be performed by preliminarily accumulating photosensitive materials, which have specific affinity to the tumor and further have photochemical reaction characteristics concerning a cellulicidal action and fluorescence caused by optical excitation, on the focus and by thereafter irradiating the photosensitive materials with light, which can be absorbed by the materials, to thereby pump or excite the photosensitive materials and to consequently generate active oxygen. FIG. 8 illustrates a laser irradiation probe of the side irradiation type that is described in the Japanese Patent Laid-open No. 63-318933/1988 Official Gazette. As shown in this figure, a conical light diffuser (namely, a conical pointed light diffuser) B made of a transparent material, to the surface A of which a scraping process or a surface roughening process is applied, is attached to a light diffuser or end portion of a light-guide (optical) fiber. With this structure, laser light emitted from the light-guide fiber passes through the inside of the light diffuser B and then reaches a side surface of the light diffuser B. As shown in FIG. 9, the surface A of the light diffuser has an uneven structure. Thus the laser light is reflected at an irregular angle in dependence on the structure of the surface where the laser light has reached, as indicated by arrows in this figure. Incidentally, reference character M denotes a tissue to be treated.

However, in the case of the aforementioned conventional probe, when a laser treatment is performed by inserting the light diffuser B thereof into an internal nallow affected part or a diseased part which is in a stenosed state, namely, the tissue M to be treated, the roughened part of the surface of the light diffuser B is stained with a humor or an internal accretion. Thus, the transmissivity, at which the laser light is transmitted, of this part of the conventional probe is deteriorated. Further, the diffusibility, by which the laser light is diffused, of this part is degraded. Consequently, the conventional probe has faced problems in that the irradiation of laser light cannot be performed in an established manner and in that a same laser irradiation probe cannot be used repeatedly.

Moreover, the conventional probe has an omnidirectional irradiation structure. Thus, the conventional probe further has encountered another problem in that even a tissue, which does not need to be irradiated with laser light, is also irradiated with laser light.

The present invention is directed to resolving the problems which the conventional probe has faced.

It is, accordingly, an object of the present invention to provide a laser irradiation probe which can realize accurate and efficient treatment and can be used repeatedly.

SUMMARY OF THE INVENTION

To achieve the foregoing object, in accordance with the present invention, there is provided a medical laser probe (hereunder sometimes referred to as a first medical laser probe of the present invention) for guiding laser light from a medical (laser) light source to an affected part to be treated, which comprises a transparent light diffuser for receiving light emitted from a light-guide fiber, which arrives from the laser light source, and for radiating the received incident light from a peripheral side surface thereof, and further comprises a protective diffusion tube, which is provided outside the peripheral side surface of the transparent light diffuser, for further diffusing laser light radiated from the transparent light diffuser.

Further, in the case of an embodiment of the first medical laser probe of the present invention, the protective diffusion tube may be detachably provided on the light diffuser.

Moreover, in the case of another embodiment of the first medical laser probe of the present invention, in addition to the aforementioned elements of the first medical laser probe, a plurality of laser-light reflection grooves are provided on the peripheral side surface of the light diffuser in such a way as to extend in a direction perpendicular to an axis of the light diffuser and in such a manner that laser light is irradiated in a direction along the axis of the light diffuser and in (radial) directions from the axis thereof to the peripheral side surface thereof.

Furthermore, in the case of still another embodiment of the first medical laser probe of the present invention, in addition to the aforementioned elements of the first medical laser probe, a plurality of dimples are formed in the peripheral side surface portion of the light diffuser in such a manner that laser light is irradiated in a direction along an axis of the light diffuser and in (radial) directions from the axis thereof to the peripheral side surface thereof.

Additionally, in the case of yet another embodiment of the first medical laser probe of the present invention, in addition to the aforementioned elements of the first medical laser probe, additive agents (namely, addition agents), which are operative to reflect laser light, are added to a transparent material of the light diffuser by gradually increasing the density of the additive agent from a laser-light incidence portion of the light diffuser to an end thereof in such a manner that the closer to the end of the light diffuser a place becomes, the higher the diffusion coefficient thereof at the place becomes, so that laser light is irradiated in a direction along an axis of the light diffuser and in (radial) directions from the axis thereof to the peripheral side surface thereof.

Further, in the case of a further embodiment of the first medical laser probe of the present invention, in addition to the aforementioned characteristic features of the first medical laser probe, the protective diffusion tube is made of translucent smooth plastics.

Moreover, in the case of another embodiment (hereunder sometimes referred to as a seventh medical laser probe of the present invention) of the first medical laser probe of the present invention, in addition to the aforementioned characteristic features of the first medical laser probe, a directivity limiting directions, in which the probe irradiates laser light, to some (radial) directions from the axis of the light diffuser to the peripheral side surface thereof is imparted to the probe. Thereby, a living body, which does not need to be irradiated with laser light, is prevented from being irradiated with laser light. For the above directivity, in this case of this embodiment of the first medical laser probe of the present invention, in addition to the aforementioned elements of the first medical laser probe, a laser-light reflector having an opening formed in a part thereof is provided between a protective diffusion tube and a transparent light diffuser.

Additionally, in the case of an embodiment of the seventh medical laser probe of the present invention, in addition to the aforementioned elements of the seventh medical laser probe, a reflector made of gold, which has high reflection efficiency and is a most stable material, is provided.

Further, in the case of another embodiment (hereunder sometimes referred to as a ninth medical laser probe of the present invention) of the first medical laser probe of the present invention, in addition to the aforementioned elements of the first medical laser probe, laser-light blocking means for blocking laser light reflected from a living body with respect to a peripheral direction of the light diffuser and leakage light leaking out of the protective diffusion tube is provided in the protective diffusion tube so as to prevent a living body, which does not need to be irradiated with laser light, from being irradiated with laser light.

Moreover, in the case of an embodiment (hereunder referred to as a tenth medical laser probe of the present invention) of the ninth medical laser probe of the present invention, in addition to the aforementioned elements of the ninth medical laser probe, the laser-light blocking means for blocking laser light is made of a fibrous material which has flexibility.

Furthermore, in the case of an embodiment of the tenth medical laser probe of the present invention, in addition to the aforementioned elements of the tenth medical laser probe, the fibrous material of the laser-light blocking means is made of a shape memory alloy.

Additionally, in the case of another embodiment (hereunder sometimes referred to as a twelfth medical laser probe of the present invention) of the first medical laser probe of the present invention, in addition to the aforementioned elements of the first medical laser probe, laser-light blocking means for blocking laser light reflected from a living body with respect to an axial direction of the light diffuser and leakage light leaking out of the protective diffusion tube are provided at both ends of the protective diffusion tube so as to prevent a living body, which does not need to be irradiated with laser light, from being irradiated with laser light.

Besides, in the case of an embodiment of the ninth or twelfth medical laser probe of the present invention, in addition to the elements of the ninth or twelfth medical laser probe of the present invention, the laser-light blocking means is made of a material adapted to block off only laser light but transmit other kinds of light so that a living body can be observed through the laser-light blocking means.

Thus, in the case of the probes of the present invention provided with the aforementioned means, laser light obtained from the light-guide fiber is diffused by the transparent light diffuser in the direction of the axis thereof and in the (radial) directions from the axis thereof to the peripheral side surface thereof. Moreover, this diffused light is further diffused by the protective diffusion tube provided outside (or on the outer surface of) the transparent light diffuser. Furthermore, the reflector having a (radial) opening formed in such a way as to extend in the direction of the axis of the light diffuser to the peripheral side surface is provided between the transparent light diffuser and the protective diffusion tube. Additionally, the laser-light blocking means is provided in the protective diffusion tube. Thereby, the efficient irradiation and the limited irradiation of laser light can be achieved.

Meanwhile, the protective diffusion tube can be detached from the probe of the present invention. When stained, the tube can be detached from the light diffuser and can be then washed separately and further can be replaced with another protective diffusion tube. Hereunder, concrete or practical embodiments of the present invention will be described.

BRIEF DESCRIPTION OF THE DRAWINGS

Other features, objects and advantages of the present invention will become apparent from the following description of preferred embodiments with reference to the drawings in which like reference characters designate like or corresponding parts throughout several views, and in which:

FIG. 6A is a front view of a primary part of this medical laser probe; and FIG. 6B is a right-hand side view of the primary part of the medical laser probe of FIG. 6A;

FIG. 7A is a front view of a primary part of this medical laser probe; and FIG. 7B is a right-hand side view of the primary part of the medical laser probe of FIG. 7A;

DETAILED DESCRIPTION OF THE PREFERRED EMBODIMENTS

First Embodiment

Hereinafter, a preferred embodiment, namely, a first embodiment according to the present invention will be described in detail by referring to the accompanying drawings.

Figure 1:
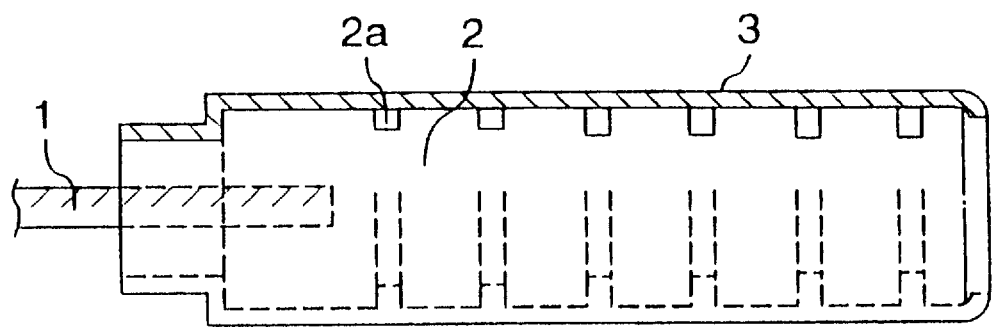
FIG. 1 is a partially sectional diagram for illustrating the configuration of a primary or principal part of a medical laser probe of the present invention.
Figure 3:
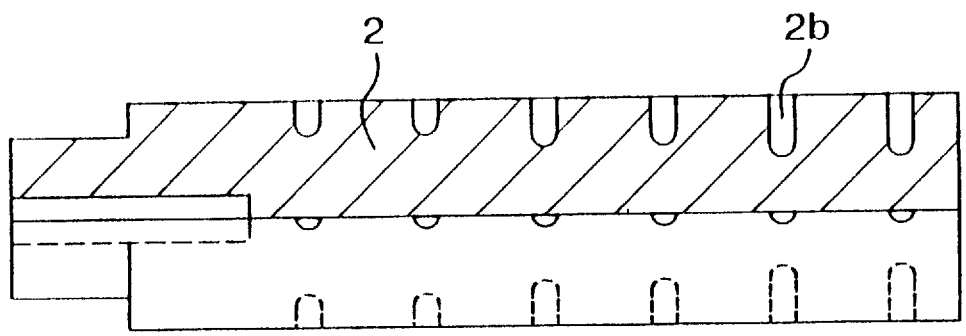
FIG. 3 is a semi sectional view of a primary part of a medical laser probe of the present invention, which illustrates the configuration of this medical laser probe provided with a dimpled transparent light diffuser.

FIG. 1 illustrates a medical laser probe of this embodiment of the present invention. In this figure, reference numeral 1 designates a light-guide fiber for guiding laser light emitted from a laser light source. Further, reference numeral 2 denotes a transparent light diffuser made of materials such as plastics, quartz and sapphire, which transmit laser light, as illustrated in FIGS. 1 and 3. In the case of the transparent light diffuser of FIG. 1, laser light is nearly uniformly diffused and radiated in the direction of the axis of the light diffuser and in the (outwardly) radial directions from the axis thereof to the peripheral surface thereof by laser-light reflection grooves 2a formed in the peripheral surface portion of the light diffuser. In the case of the transparent light diffuser of FIG. 3, similarly, laser light is nearly uniformly diffused and radiated in such directions by dimples 2b. Moreover, reference numeral 3 designates a protective diffusion tube made of translucent plastics, which is operative to further diffuse laser light diffused and radiated by the transparent light diffuser 2. Furthermore, inorganic additive agents, which are operative to reflect laser light, may be added to the material of the transparent light diffuser, which transmits laser light, instead of providing the laser-light reflection grooves 2a or the dimples 2b in the light diffuser. At that time, the additive agent may be added thereto so that the closer to the (pointed) end of the light diffuser a place becomes, the higher the density of the additive agent becomes.

Figure 2:
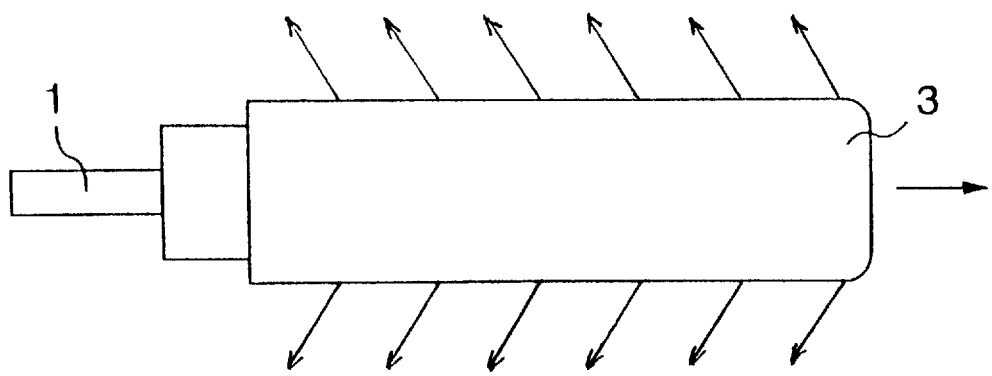
FIG. 2 is a front view of the primary part of the medical laser probe of the present invention, which illustrates how laser light is radiated from the medical laser probe of the present invention.

When laser light is incident on the laser probe constructed as above described, the laser light travels in the transparent light diffuser 2 at an angle, at which the laser light is radiated from the light-guide fiber 1, from the axis thereof. Then, the laser light impinges on the laser reflection grooves 2a, the dimples 2b or the additive agents for reflecting laser light. Thus, the laser light undergoes a complex transmission/reflection process. After this complex transmission/reflection process, the laser light is radiated from the transparent light diffuser 2 and is then incident on the protective diffusion tube 3 provided outside the light diffuser 2. Subsequently, the incident laser light is further diffused owing to the diffusibility thereof in the protective diffusion tube 3 made of translucent plastics. Then, the diffused laser light is radiated from the tube 3 as indicated by arrows in FIG. 2. Further, the surface of the protective diffusion tube is smooth, so that the surface thereof is hardly stained with deposits. Even when stained, the deposits can easily be wiped away therefrom. If necessary, the tube can be replaced with another protective diffusion tube.

Second Embodiment

Hereinafter, another medical laser probe, which has directivity, according to the present invention, namely, a second embodiment of the present invention will be described by referring to the accompanying drawings.

Figure 4:
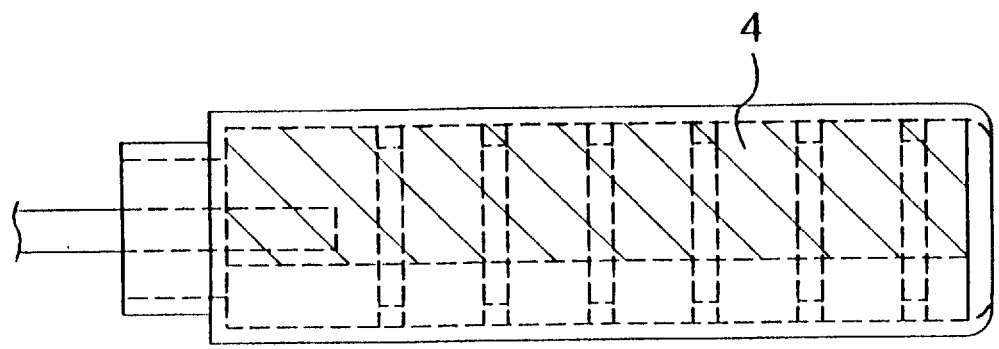
FIG. 4 is a front view of a primary part of a medical laser probe of the present invention, which illustrates the configuration of this medical laser probe provided with a reflector.

FIG. 4 illustrates the medical laser probe, which has directivity, of this embodiment. In this figure, reference numeral 4 designates a laser-light reflector which is provided between the transparent light diffuser and the protective diffusion tube of the medial laser probe and which has an opening made therein in such a manner that the opening directs to a direction where laser light is irradiated.

When laser light is incident on the laser probe constructed as above described, the laser light travels in the transparent light diffuser 2 at an angle, at which the laser light is radiated from the light-guide fiber 1, from the axis thereof. Then, the laser light impinges on the laser reflection grooves 2a, the dimples 2b or the additive agents for reflecting laser light, which are provided in the transparent light diffuser 2. Thus, the laser light undergoes a complex transmission/reflection process. After this complex transmission/reflection process, the laser light is radiated from the transparent light diffuser 2 and is then incident on the protective diffusion tube 3, which is provided outside the light diffuser 2, in the case that the reflector 4 is not present at a place, from which the laser light is radiated, on the light diffuser 2 and this place coincides with the position of the opening. Subsequently, the incident laser light is further diffused by the protective diffusion tube 3. Then, the diffused laser light is radiated from the tube 3. In contrast, when laser light impinges on the reflector 4, the laser light is reflected at an angle which depends on the angle of incidence of the laser light. Subsequently, the reflected laser light impinges on the transparent light diffuser 2 again. Further, the laser light having impinged on the transparent light diffuser 2 goes through a complex reflection process. Finally, the laser light is radiated from the opening through the protective diffusion tube 3.

Consequently, laser light can be concentrated on only a part or region which requires a laser treatment. Thereby, a highly efficient treatment can be provided.

Figure 5:
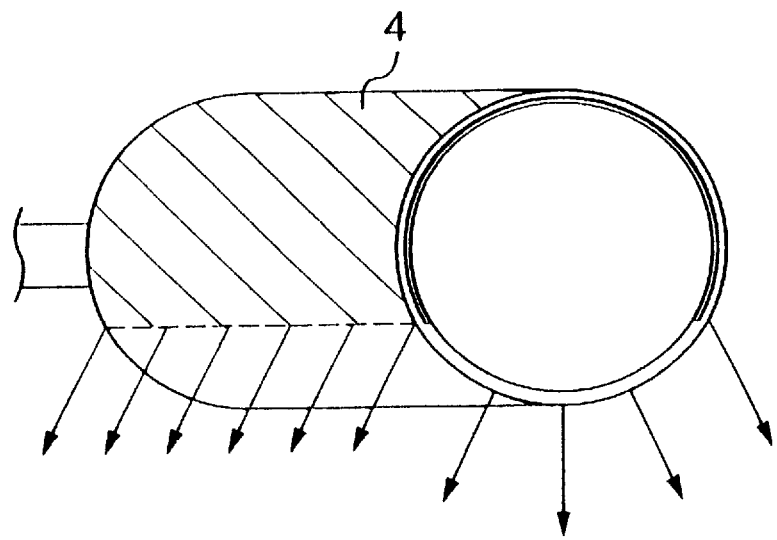
FIG. 5 is a perspective view of the primary part of the medical laser probe of the present invention, which illustrates how laser light is radiated from the medical laser probe provided with the reflector.

Incidentally, the reflector 4 may be shaped like a rectangle or mounted on the outer surface of the protective diffusion tube 5, as illustrated in FIG. 5. Further, the reflector 4 may be preferably made of gold that is chemically stable.

Third Embodiment

Hereinafter, still another medical laser probe, which has a shielding capability, according to the present invention, namely, a second embodiment of the present invention will be described by referring to the accompanying drawings.

Figure 6A:
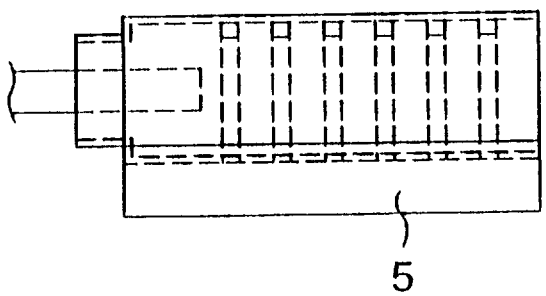
FIGS. 6A and 6B illustrate the configuration of a medical laser probe of the present invention provided with shielding plates, namely.
Figure 6B:
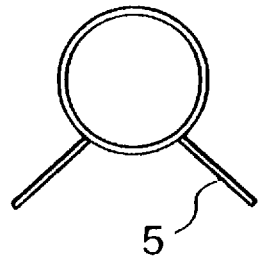

FIGS. 6A and 6B illustrate a medical laser probe, which has a shielding capability, of the present invention. In these figures, reference numeral 5 designates shielding plates. Further, as illustrated in these figures, two flexible shielding plates are provided along the axis of the laser probe in such a way as to be adjusted to the laser opening of the medical laser probe described in the description of the aforementioned second embodiment of the present invention. Alternatively, shielding matters, which are made of fibrous materials and arranged in a line, are provided in the probe in a similar manner, instead of the shielding plates.

Figure 7A:
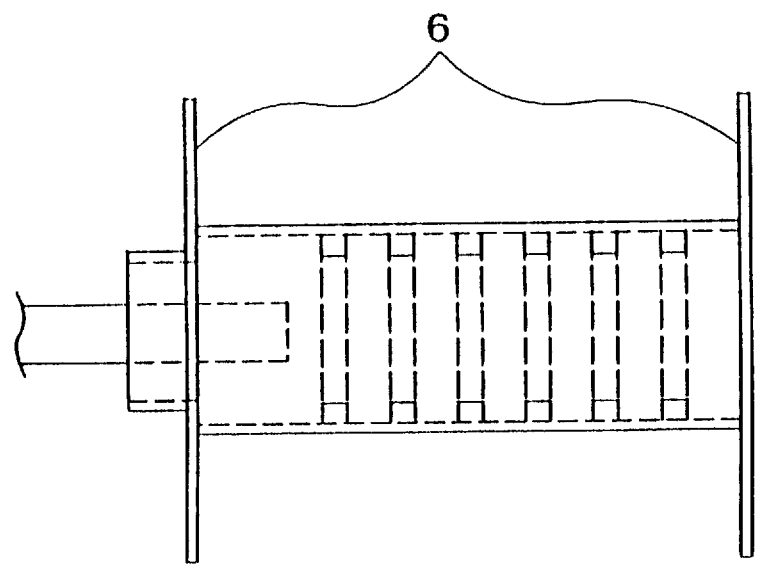
FIGS. 7A and 7B illustrate the configuration of another medical laser probe of the present invention provided with shielding plates, namely.
Figure 7B:
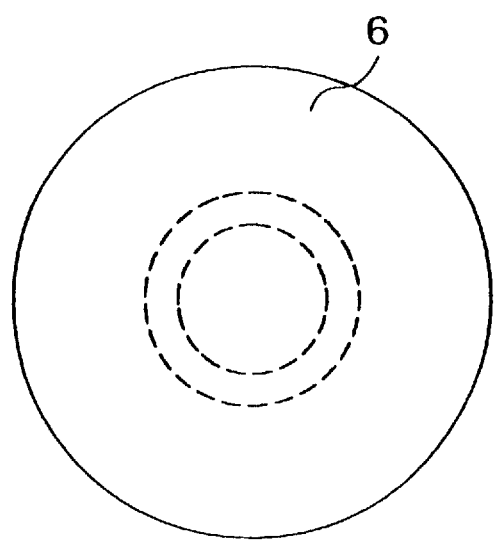
Figure 8:
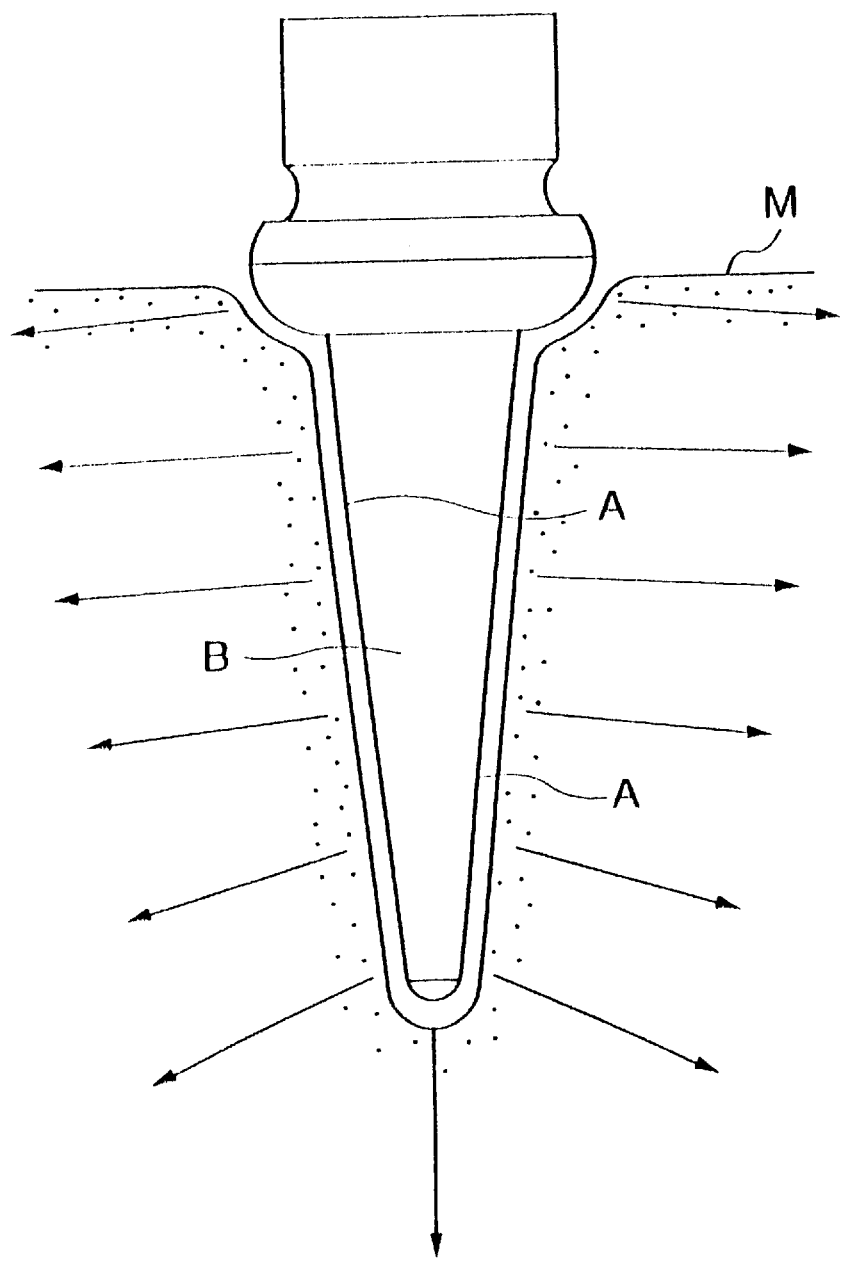
FIG. 8 is a diagram for illustrating a prior art medical laser probe.
Figure 9:
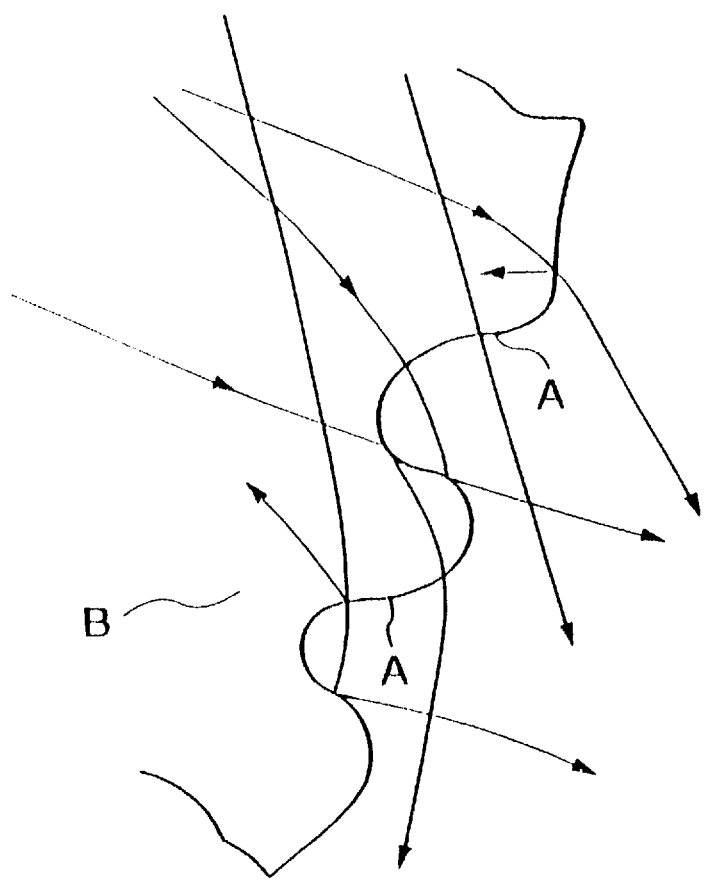
FIG. 9 is an enlarged view of a surface of the transparent light diffuser of the prior art medical laser probe.

Further, FIGS. 7A and 7B illustrate another medical laser probe that also has the shielding capability. In these figures, reference numeral 6 designates shielding plates for blocking off laser light. These shielding plates are provided at two places, namely, at an end and at the opposite light-guide-fiber-side end of the medical laser probe as described in the descriptions of the aforementioned first and second embodiments.

When laser light is radiated from the laser probe constructed as above described and a living body, for example, a trachea is irradiated with the radiated laser light, generally, 60 percent of the irradiated laser light is incident on the inside of the living body and 40 percent thereof is reflected on the surface of the living body. If the aforementioned shielding plates 5 and 6 were not provided, the reflected laser light would undergo a complex reflection process in the trachea, so that not only an affected part to be treated but also a normal part would be widely irradiated with the laser light. Namely, the laser light would reach the normal part that does not require medical treatment. The shielding plates 5 and 6 serve to prevent the reflected laser light from straying into a normal part. The shielding plates may be shaped like a disk.

Further, by selecting a material, by which only light, whose wavelength is within the wavelength band of the laser light, is blocked off, as the material of the shielding plates, a diseased part to be treated can be observed without being obstructed by the shielding plates. Incidentally, if the aligned shielding matters made of fibrous materials are used instead of the shielding plates, it is more advantageous because the probe can be smoothly taken out of and into an endoscope without resistance or disturbance.

As described hereinabove, in accordance with those embodiments, laser light is obtained or radiated in the direction of the axis of the light diffuser and in the radial directions from the axis thereof to the peripheral side surface thereof. Further, the surface of the protective diffusion tube is smooth and resists soiling. Even if soiled, stains can easily be wiped out. Moreover, the protective diffusion tube can be detached from the light diffuser. Furthermore, it is possible to replace only the protective diffusion tube with another protective diffusion tube. Consequently, accurate laser treatment can be achieved. Moreover, the medical laser probe can be used repeatedly.

Furthermore, the provision of the reflector in the probe enables the concentration of laser light. Thus, the effective utilization of laser light can be achieved.

Additionally, the provision of the shielding plates, which are used for blocking off laser light, in a probe enables the probe to prevent laser light from being applied to a part other than affected parts to be treated.

Although the preferred embodiments of the present invention have been described above, it should be understood that the present invention is not limited thereto and that other modifications will be apparent to those skilled in the art without departing from the spirit of the invention.

The scope of the present invention, therefore, should be determined solely by the appended claims.

What is claimed is:

1. A medical laser probe for guiding laser light from a treatment light source to an affected body part to be treated, comprising:
    a transparent light diffuser for receiving light emitted from a light-guide fiber, which is provided from the treatment light source, and for radiating the received light from a peripheral surface thereof; and
    a protective diffusion tube, which is provided outside the peripheral surface of the transparent light diffuser, for further diffusing light radiated from the transparent light diffuser, said light diffuser having on said peripheral surface a plurality of laser-light reflection grooves which are provided on the peripheral surface of said light diffuser and are oriented in a direction perpendicular to a longitudinal axis of the light diffuser such that light irradiating in a direction along said longitudinal axis of the light diffuser and in radial directions from said longitudinal axis is radially and evenly reflected in a direction opposite said longitudinal axis of the light diffuser to the peripheral surface of said light diffuser.

2. The medical laser probe according to claim 1, wherein the protective diffusion tube is detachably provided on the light diffuser.

3. The medical laser probe according to claim 1, wherein additive agents, which are operative to reflect laser light, are added to a transparent material of the light diffuser by gradually increasing a density of the additive agent from a laser-light incidence portion of the light diffuser to an end portion of the light diffuser such that the light diffuser has an increasing diffusion coefficient from said incidence portion to said end portion, so that light is irradiated in a direction along a longitudinal axis of the light diffuser and in radial directions from the longitudinal axis to the peripheral surface of the light diffuser.

4. The medical laser probe according to claim 1, wherein the protective diffusion tube is made of translucent smooth plastics.

5. The medical laser probe according to claim 1, wherein a laser-light reflector shaped like a rectangle is inserted between the protective diffusion tube and the transparent light diffuser along the axis of the light diffuser so that a part, which does not need to be irradiated with laser light, is shielded from laser light radiated in the radial directions from the axis of the light diffuser to the peripheral side surface thereof and that laser light radiated in the radial directions from the axis of the light diffuser to the peripheral side surface thereof is concentrated onto a part to be irradiated with laser light.

6. The medical laser probe according to claim 5, wherein the reflector is made of gold which has high efficiency in reflecting laser light.

7. The medical laser probe according to claim 1, which further comprises flexible laser-light blocking means mounted outside the protective diffusion tube and along an axis thereof.

8. The medical laser probe according to claim 7, wherein the laser-light blocking means is made of a fibrous material having flexibility.

9. The medical laser probe according to claim 8, wherein the fibrous material of the laser-light blocking means is made of a shape memory alloy.

10. The medical laser probe according to claim 7, wherein the laser-light blocking means is made of a material adapted to selectively block off laser light and to transmit light other than laser light.

11. The medical laser probe according to claim 1, which further comprises disk-like flexible laser-light blocking means mounted at both ends of the protective diffusion tube in such a manner that each of the laser-light blocking means extends in a direction perpendicular to an axis of the protective diffusion tube.

12. The medical laser probe according to claim 11, wherein the laser-light blocking means is made of a material adapted to selectively block off laser light and to transmit light other than laser light.

13. The medical laser probe according to claim 1, wherein said grooves have progressively increasing depths toward a distal end of the light diffuser.

14. A medical laser probe for guiding laser light from a treatment light source to an affected body part to be treated, comprising:
    a transparent light diffuser for receiving light emitted from a light-guide fiber, which is provided from the treatment light source, and for radiating the received light from a peripheral surface thereof; and
    a protective diffusion tube, which is provided outside the peripheral surface of the transparent light diffuser, for further diffusing light radiated from the transparent light diffuser, wherein a plurality of dimples are formed in said peripheral surface of the light diffuser and are oriented in a direction perpendicular to a longitudinal axis of the light diffuser such that light irradiating in a direction along a longitudinal axis of the light diffuser and in radial directions from said longitudinal axis is radially and evenly reflected in an outward direction opposite said longitudinal axis of the light diffuser to the peripheral surface of said light diffuser.

15. The medical laser probe according to claim 14, wherein the protective diffusion tube is detachably provided on the light diffuser.

16. The medical laser probe according to claim 14, wherein additive agents, which are operative to reflect laser light, are added to a transparent material of the light diffuser by gradually increasing a density of the additive agent from a laser-light incidence portion of the light diffuser to an end of the light diffuser such that the light diffuser has an increasing diffusion coefficient from said incidence portion to said end portion, so that light is irradiated in a direction along a longitudinal axis of the light diffuser and in radial directions from the longitudinal axis to the peripheral surface of the light diffuser.

17. The medical laser probe according to claim 14, wherein the protective diffusion tube is made of translucent smooth plastics.

18. The medical laser probe according to claim 14, wherein said dimples have progressively increasing depths toward a distal end of the light diffuser.

* * * * *